(12) United States Patent
Shoemake

(10) Patent No.: US 7,112,343 B1
(45) Date of Patent: Sep. 26, 2006

(54) IMMUNE SYSTEM RECONSTRUCTOR COMPOSITION

(76) Inventor: Robbie Shoemake, 2340 Crisp Springs Rd., McMinnville, TN (US) 37110

( * ) Notice: Subject to any disclaimer, the term of this patent is extended or adjusted under 35 U.S.C. 154(b) by 295 days.

(21) Appl. No.: 10/852,718

(22) Filed: May 24, 2004

(51) Int. Cl.
*A01N 65/00* (2006.01)

(52) U.S. Cl. ................ 424/726; 424/725; 424/730; 424/735; 424/752; 424/754; 424/769; 424/773; 424/774; 424/775; 424/778; 424/779

(58) Field of Classification Search ............... None
See application file for complete search history.

(56) References Cited

U.S. PATENT DOCUMENTS

| | | | |
|---|---|---|---|
| 4,719,111 A | 1/1988 | Wilson | |
| 4,737,364 A | 4/1988 | Kalogris | |
| 5,876,728 A | 3/1999 | Kass et al. | |
| 5,976,548 A | 11/1999 | Hsia et al. | |
| 5,989,560 A | 11/1999 | Terry et al. | |
| 6,086,886 A | 7/2000 | Guo | |
| 6,180,106 B1 | 1/2001 | Keller et al. | |
| 6,264,995 B1 | 7/2001 | Newmark et al. | |
| 6,280,751 B1 * | 8/2001 | Fletcher et al. | 424/401 |
| 6,312,736 B1 | 11/2001 | Kelly et al. | |
| 6,399,114 B1 | 6/2002 | Foreman | |
| 6,426,099 B1 | 7/2002 | Terry et al. | |
| 6,432,455 B1 | 8/2002 | Keller et al. | |
| 6,737,089 B1 * | 5/2004 | Wadsworth et al. | 424/777 |
| 2005/0002962 A1 * | 1/2005 | Pasco et al. | 424/195.15 |
| 2005/0008690 A1 * | 1/2005 | Miller | 424/451 |
| 2005/0025737 A1 * | 2/2005 | Sebagh | 424/74 |

OTHER PUBLICATIONS

Internet Product Listing entitled "Bulk Botanical Products" from iwebsite naturescathedral, 8 pages, downloaded Mar. 22, 2006.*

* cited by examiner

*Primary Examiner*—Christopher R. Tate
(74) *Attorney, Agent, or Firm*—Michael I Kroll

(57) ABSTRACT

The present invention discloses an all natural composition comprising herbs for the use of restoring the immune system and subsequent medicinal value. The formulization of the present invention utilizes the benefits of herbal medicine for the use of restoring the immune system to protect and cure the body from infectious disease and various allergies. The composition formula consists of nineteen herbal ingredients in powder form that carrot powder, pau d' arco bark, *gingko* leaf, myrrh bark, *echinacea* augusta folia, slippery elm bark, heal-all-herb, celery stalk, celery leaf, red clover blooms, burdock root, goldenseal root, poke root, garlic bulb powder, beet root powder, yellow dock root, dandelion root, St. John's wort, and capsicum in predetermined quantities.

6 Claims, 8 Drawing Sheets

IMMUNE SYSTEM RECONSTRUCTOR FORMULATION

10

| | | |
|---|---|---|
| 12 — CARROT POWDER | 29 | PARTS |
| 14 — PAU D' ARCO BARK | 27 | PARTS |
| 16 — GINGKO LEAF | 19 | PARTS |
| 18 — MYRRH BARK | 19 | PARTS |
| 20 — ECHINACEA AUGUSTAFOLIA | 17 | PARTS |
| 22 — SLIPPERY ELM BARK | 15 | PARTS |
| 24 — HEAL-ALL-HERB | 15 | PARTS |
| 26 — CELERY STALK | 14 | PARTS |
| 28 — CELERY LEAF | 14 | PARTS |
| 30 — RED CLOVER BLOOMS | 13 | PARTS |
| 32 — BURDOCK ROOT | 11 | PARTS |
| 34 — GOLDENSEAL ROOT | 10 | PARTS |
| 36 — POKE ROOT | 9 | PARTS |
| 38 — GARLIC BULB POWDER | 7 | PARTS |
| 40 — BEET ROOT POWDER | 7 | PARTS |
| 42 — YELLOW DOCK ROOT | 6 | PARTS |
| 44 — DANDELION ROOT | 6 | PARTS |
| 46 — ST. JOHN'S WORT | 4 | PARTS |
| 48 — CAPSCIUM | 0.5 | PARTS |

IMMUNE SYSTEM RECONSTRUCTOR COMPOSITION

BACKGROUND OF THE INVENTION

Field of the Invention

The present invention relates generally to an all natural composition and, more specifically, to an all natural composition comprised of herbs for the use of restoring the immune system and subsequent medicinal value.

An herb is a plant or plant part valued for its medicinal, aromatic or savory qualities. Herb plants produce and contain a variety of chemical substances that act upon the body. Herbal medicine, sometimes referred to as herbalism or botanical medicine, is the use of herbs for their therapeutic or medicinal value.

Herbal medicine is the oldest form of healthcare known to mankind. Herbs had been used by all cultures throughout history. It was an integral part of the development of modern civilization. The plants provided food, clothing, shelter, and medicine. Much of the medicinal use of plants seems to have been developed through observations of wild animals, and by trial and error.

Methodically, information was collected on herbs and well-defined herbal pharmacopoeias were developed. Many drugs commonly used today are of herbal origin. Some are made from plant extracts; others are synthesized to mimic a natural plant compound.

The World Health Organization (WHO) estimates that 4 billion people, 80 percent of the world population, presently use herbal medicine for some aspect of primary health care. Herbal medicine is a major component in all indigenous peoples' traditional medicine and a common element in traditional oriental and Native American Indian medicine.

The formulization of the present invention utilizes the benefits herbal medicine for the use of restoring the immune system. In restoring the immune system, the present invention formulization provides means to protect and cure the body from infectious disease and various allergies.

A properly functioning immune system is a well-trained and disciplined biological warfare unit for the body. It is able to identify and destroy many foreign invaders. The immune system can also identify cells that are infected internally with viruses, as well as many cells that are on their way to becoming tumors. It does all of this work so the body remains healthy.

In restoring the immune system, the present invention formulization can be both, a preventive medicine and a healing treatment for allergic reactions. Many people suffer from seasonal, respiratory allergies, usually in the spring or fall and caused by pollen and mold. Some people suffer from food allergies. Of injected allergens, penicillin and insect venom are common offenders.

The present invention, the formula consists of nineteen herbal ingredients in powder form. These ingredients include carrot powder, pau d' arco bark, *gingko* leaf, myrrh bark, *echinacea* augusta folia, slippery elm bark, heal-all-herb, celery stalk, celery leaf, red clover blooms, burdock root, goldenseal root, poke root, garlic bulb powder, beet root powder, yellow dock root, dandelion root, St. John's wort, and capsicum.

With the preferred embodiment of the present invention, the formula consists of nineteen herbal ingredients in powder form in the following measurement. These ingredients include: 29 parts—carrot powder, 27 parts—pau d' arco bark, 19 parts—*gingko* leaf, 19 parts—myrrh bark, 17 parts—*echinacea* augusta folia, 15 parts—slippery elm bark, 15 parts B heal-all-herb, 14 parts—celery stalk, 14 parts—celery leaf, 13 parts—red clover blooms, 11 parts—burdock root, 10 parts B goldenseal root, 9 parts—poke root, 7 parts—garlic bulb powder, 7 parts—beet root powder, 6 parts—yellow dock root, 6 parts—dandelion root, 4 parts—St. John's wort, and ½ parts—capscium.

A preferred further element of the present invention includes the equivalent formulation said powder form prepared and packaged ready for consumption. The powder form may consist in tablet or pellet form, capsulated, or added to a liquid in the form of a drink mix or poultice.

2. Description of the Prior Art

There are other herbal compositions formulated for consumption. Typical of these is U.S. Pat. No. 4,719,111 issued to Lynn M. Wilson on Jan. 12, 1988.

Another patent was issued to Theodore P. Kalogris on Apr. 12, 1988 as U.S. Pat. No. 4,737,364. Yet another U.S. Pat. No. 5,876,728 was issued to Howard David Kass on Mar. 2, 1999.

Another was issued on Nov. 2, 1999 to Houn Simon Hsia as U.S. Pat. No. 5,976,548. Yet another was issued to Travis L. Terry on Nov. 23, 1999 as U.S. Pat. No. 5,989,560. Still yet another was issued to Peilin Guo on Jul. 11, 2000 as U.S. Pat. No. 6,086,886.

Another was issued on Jan. 30, 2001 to Robert H Keller as U.S. Pat. No. 6,180,106. Yet another was issued to Thomas Newmark on Jul. 24, 2001 as U.S. Pat. No. 6,264,995.

Still yet another was issued to Gregory J. Kelly on Nov. 6, 2001 as U.S. Pat. No. 6,312,736. Another was issued on Jun. 4, 2002 to David J. Foreman as U.S. Pat. No. 6,399,114.

Yet another was issued to Travis L. Terry on Jul. 30, 2002 as U.S. Pat. No. 6,426,099. Still yet another was issued to Robert H. Keller on Aug. 13, 2002 as U.S. Pat. No. 6,432,455.

This invention related to a novel composition for treatment of decubitus ulcers. A composition for treatment of decubitus ulcers comprising an admixture of from about 10 to about 50 parts lecithin, from about 10 to about 50 parts goldenseal root or rhizome, and from about 10 to about 50 parts myrrh gum.

This invention relates to a highly nutritional dry food concentrate consisting entirely of plant and other non-animal natural components having a low caloric content and containing no added simple sugars. The nutritional dry food concentrate consisting entirely of natural ingredients is useful as a food supplement and in a weight reduction program.

This invention relates to a method of treating cancer comprising administering an effective amount of either a composition of three herbal extracts consisting essentially of 30% to 70% by weight Goldenseal, 20% to 40% by weight of Myrtle, and 5% to 20% by weight of Centaurea, or a composition of seven herbal extracts consisting essentially of 3% to 5% by weight Centaurea, 1.5% to 4% by weight Capsicum, 1.5% to 4% by weight Lobelia, 20% to 40% by weight Myrrh, 30% to 50% by weight Echinacea, 15% to 25% by weight Goldenseal, and 3% to 5% by weight Myrtle. The compositions were prepared by separately extracting each herb by mixing the herb in water, ethyl alcohol, or a mixture of water and ethyl ether, boiling and cooling the mixture, allowing the mixture to stand for about two weeks, filtering the mixture to obtain the liquid phase, and combining each of said extracts to obtain said compositions.

This invention relates to nutritional supplements to the human diet used to increase levels of high density lipoprotein (HDL) and calcium ions, and decrease levels of free radicals and glucose in human blood plasma. More specifically, the present invention teaches novel nutritional supplements which comprise a novel combination of specific antioxidants, barley grass extract, specific multiple vitamins and minerals, and *ginkgo biloba* extract, as well as methods of preparing the nutritional supplements.

This invention relates to an herbal formulation comprising a liquid component and a solid component. The liquid component comprises black walnut, wormwood, clove, orange peel, and marshmallow. The solid component comprises wormwood, black walnut, quassia, clove, pumpkin seed, deodorized garlic, pippli, cascara sagrada, calcium undecylenate, caprylic acid, pau d'arco, rosemary oil, thyme, bismuth citrate, and grapefruit seed.

This invention relates to an herbal formulation comprising a liquid component and a solid component. The liquid component comprises black walnut, wormwood, clove, orange peel, and marshmallow. The solid component comprises wormwood, black walnut, quassia, clove, pumpkin seed, deodorized garlic, pippli, cascara sagrada, calcium undecylenate, caprylic acid, pau d'arco, rosemary oil, thyme, bismuth citrate, and grapefruit seed.

This composition relates to a unique formulation of Traditional Chinese Medicine (TCM) extracts created to reduce the debilitating symptoms of allergies. It combines a number of organically grown, but, non-organically extracted, standardized formulations of natural ingredients which have been used singly for hundreds of years for symptomatic relief of allergies. These include Ginseng and Gan Cao, which provide a natural anti-inflammatory effect; Bai Gao, which prevent the smooth muscle spasms associated with allergic reactions; Suan Zao ren, which provides an antihistamine effect without the usual sedative effect; and Wu Mai, which reduces the local swelling associated with allergies. Combined, it was unexpectedly found that these ingredients provide a natural, non-drying, non-sedating alternative to antihistamines, without inhibiting the natural healing mechanisms.

This invention relates to an herbal composition for reducing inflammation in bones and joints by inhibiting the enzyme cyclooxygenase-2 is prepared from holy basil, turmeric, ginger, green tea, rosemary, huzhang, Chinese goldthread, barberry, oregano and scutellariae baicalensis. More particularly, the herbal composition of the present invention contains therapeutically effective amounts of the supercritical extracts of ginger, rosemary and oregano, and therapeutically effective amounts of extracts of holy basil, turmeric, green tea, huzhang, Chinese goldthread, barberry, rosemary and scutellariae baicalensis. The herbal composition can be administered orally, topically or parenterally. Particularly preferred embodiments are soft gel capsules for oral administration and creams for topical application. In addition to reducing inflammation, the herbal composition also promotes healthy joint function and, because it inhibits cyclooxygenase-2 (COX-2), the composition also promotes normal cell growth. Furthermore, the herbal composition contains organic anti-aging constituents that inactivate oxygen free radicals, thereby providing antioxidant benefits in addition to anti-inflammatory benefits.

This invention relates to an herbal composition used to relieve pain and other symptoms associated with migraines and other types of headaches. The preferred herbal composition includes white willow bark extract, kava kava root extract, feverfew extract, ginger root extract, Guarana extract, and Vitamin B6. The herbal composition may be combined with liposomes to carry the composition. The result is an herbal composition that can be applied sublingually for rapid, effective pain relief.

This invention relates to a novel composition for treating nervous system disorders. The composition is formed by preparing a mixture comprising an effective amount of vitamin B-6, folic acid, vitamin C, magnesium, vitamin B-3, copper, probiotics, fructo-oligosaccharide (FOS), betaine, pancreatin, papain, pepsin, vitamin B-1, vitamin B-2, vitamin B-12, biotin, pantothenic acid, chromium polynicotinate and a digestive support ingredient selected from the group consisting of dandelion root, juniper, aloe vera, burdock, ginger root, artichoke, and kelp. Other ingredients may include: beta carotene, vitamin E, selenium, zinc, sea vegetation, alfalfa, trace minerals and molybdenum.

This invention relates to an herbal formulation comprising betaine HCl, plant enzymes, papain, probiotic micro flora, fruitooligosaccharides, 1-glutamine, quercitin, butyric acid, borage seed, flax seed, lecithin, gamma oryzanol, bromelain, pepsin, and N-acetylglucosamine.

This invention relates to a unique formulation of Traditional Chinese-Medicine (TCM) extracts created to reduce the debilitating symptoms of allergies. It combines a number of organically grown, but, non-organically extracted, standardized formulations of natural ingredients which have been used singly for hundreds of years for symptomatic relief of allergies. These include Ginseng and Gan Cao, which provide a natural anti-inflammatory effect; Bai Gao, which prevent the smooth muscle spasms associated with allergic reactions; Suan Zao ren, which provides an antihistamine effect without the usual sedative effect; and Wu Mai, which reduces the local swelling associated with allergies. Combined, it was unexpectedly found that these ingredients provide a natural, non-drying, non-sedating alternative to antihistamines, without inhibiting the natural healing mechanisms.

While these herbal compositions may be suitable for the purposes for which they were designed, they would not be as suitable for the purposes of the present invention, as hereinafter described.

SUMMARY OF THE PRESENT INVENTION

A primary object of the present invention is to provide an herbal composition that restores the body's immune system.

Another object of the present invention is to provide an herbal composition that can be utilized as a healing treatment.

Yet another object of the present invention is to provide an herbal composition that can be utilized as a preventive medicine.

Still yet another object of the present invention is to provide an herbal composition that can be utilized as a healing treatment of infectious disease.

Yet another object of the present invention is to provide an herbal composition that can be utilized as a healing treatment of allergic reactions.

Another object of the present invention is to provide an herbal composition that can be utilized as a preventive medicine to protect against infectious disease.

Still another object of the present invention is to provide an herbal composition that can be utilized as a preventive medicine to protect against allergies.

Another object of the present invention is to provide an herbal composition that is cost effective to manufacture and to consume.

Yet another object of the present invention is to provide an herbal composition that is prepackaged and readied for consumption.

Additional objects of the present invention will appear as the description proceeds.

The present invention overcomes the shortcomings of the prior art by providing a herbal composition that restores a strong and healthy immune system that allows the body to cure infectious disease and allergic reaction.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which:

FIG. 1 is a block diagram of the present invention formula for immune system reconstruction;

DESCRIPTION OF THE REFERENCED NUMERALS

Figure 2:
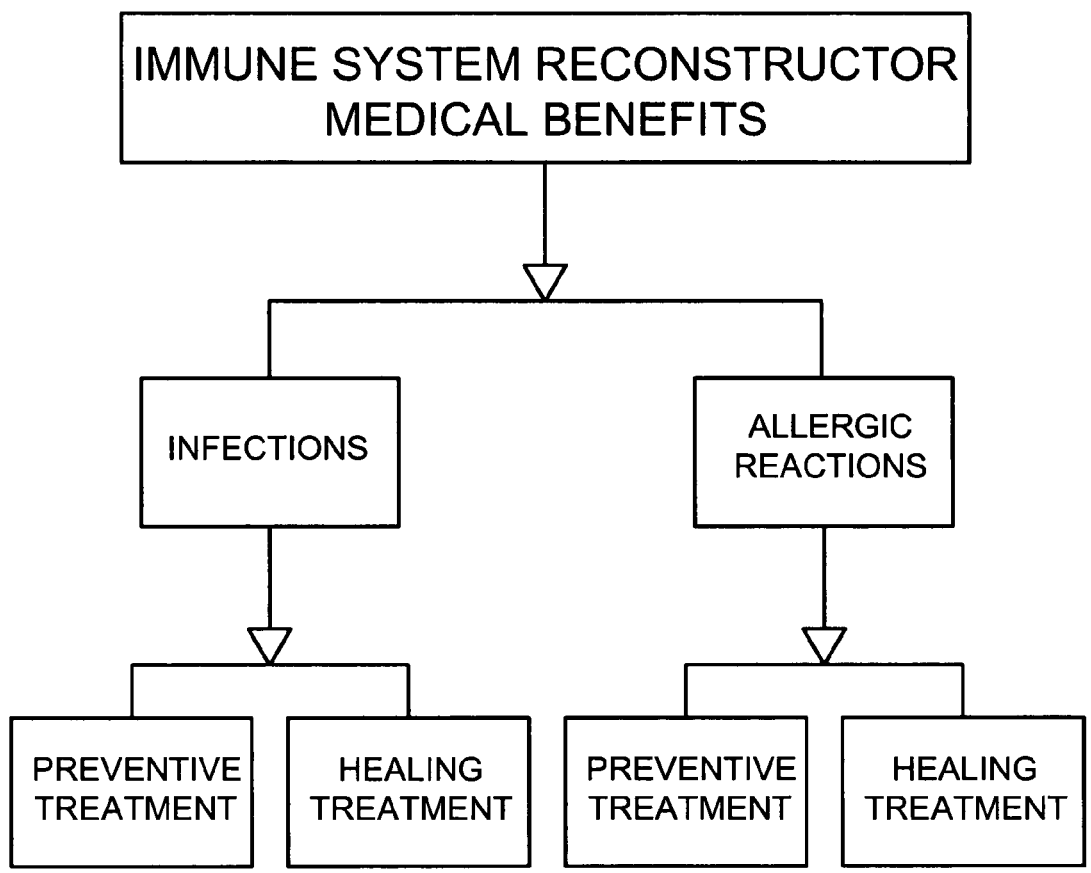
FIG. 2 is a block diagram of the present invention, immune system reconstructor medical benefits.

Turning now descriptively to the drawings, in which similar reference characters denote similar elements throughout the several views, the Figures illustrate the 3 dimensional TV system of the present invention. With regard to the reference numerals used, the following numbering is used throughout the various drawing figures.

10 Immune System Reconstructor Composition
12 carrot powder
14 pau d' arco bark
16 *gingko* leaf
18 myrrh bark
20 *echinacea* augustafolia
22 slippery elm bark
24 heal-all-herb
26 celery stalk
28 celery leaf
30 red clover blooms
32 burdock root
34 goldenseal root
36 poke root
38 garlic bulb powder
40 beet root powder
42 yellow dock root
44 dandelion root
46 St. John's wort
48 capscium
50 water
52 medical benefits block diagram
54 infectious treatment block diagram
56 allergic treatment block diagram
58 formulation types block diagram
60 pelletizing process block diagram
62 encapsulation process block diagram
64 drink mix

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

Referring to FIG. 1, shown is a block diagram of the ingredients of the present invention. The immune system reconstructor (10) is formulated from all natural products consisting of various herbs. The special formulated blend of the immune system reconstructor (10) is comprised of nineteen herbal ingredients in powder form in the following measurement. These ingredients include: 29 parts—carrot powder (12), 27 parts—pau d' arco bark (14), 19 parts—*gingko* leaf (16), 19 parts—myrrh bark (18), 17 parts—*echinacea* augustafolia (20), 15 parts—slippery elm bark (22), 15 parts—heal-all-herb (24), 14 parts—celery stalk (26), 14 parts—celery leaf (28), 13 parts—red clover blooms (30), 11 parts—burdock root (32), 10 parts—goldenseal root (34), 9 parts—poke root (36), 7 parts—garlic bulb powder (38), 7 parts—beet root powder (40), 6 parts—yellow dock root (42), 6 parts—dandelion root (44), 4 parts—St. John's wort (46), and ½ parts—capscium (48). The herbs can provide the user a restored immune system that is essential to protecting the body against infectious diseases.

Referring to FIG. 2, shown is a block diagram of the present invention, immune system reconstructor medical benefits (52). The immune system reconstructor (10) can be effective in protecting against infectious diseases and allergic reactions. In addition, the immune system reconstructor is formulated to provide both a preventive medicine and a healing treatment.

Figure 3:
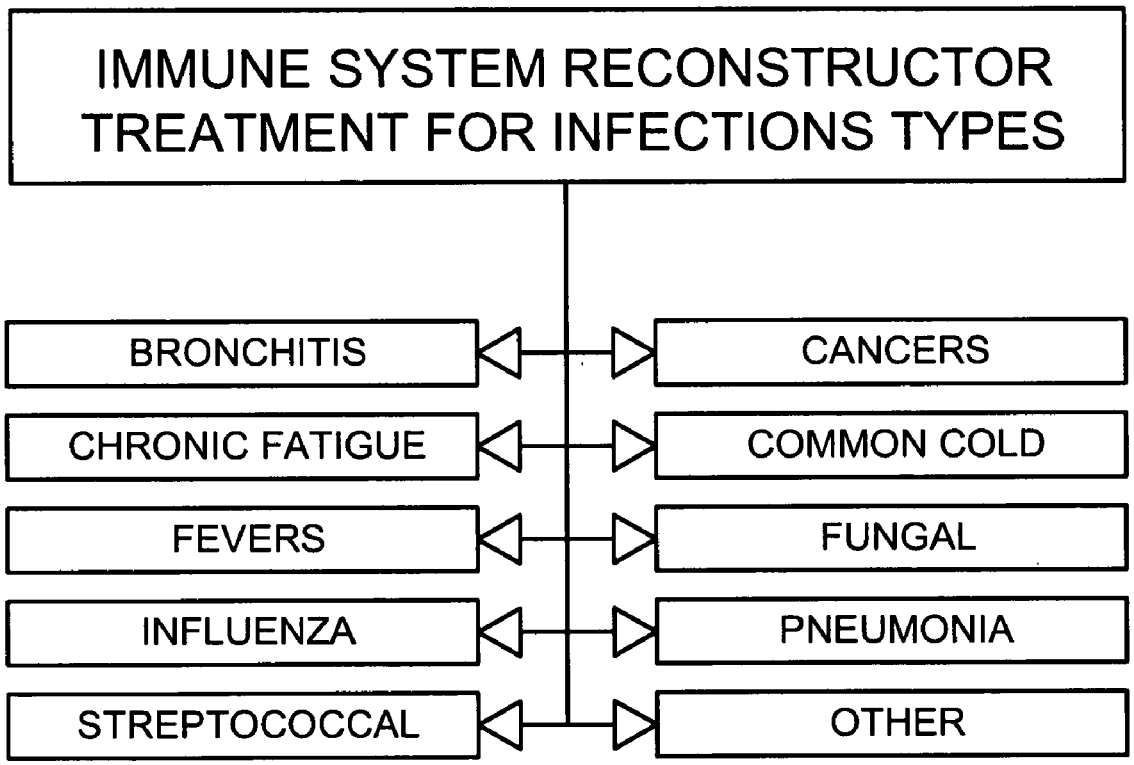
FIG. 3 is a block diagram of the present invention, immune system reconstructor treatment for infection types.

Referring to FIG. 3, shown is a block diagram of bodily disorders (54) that can benefit from a stronger immune system. The immune system reconstructor (10) can be used to improve the body's natural immune system by providing a naturally occurring herbal mixture for human consumption. A strong immune system is essential to protecting against and being cured from infectious diseases. Infectious diseases such as illustrated can be fought and cured by restoring a strong immune system. The formulation of the present invention provides the user an all natural means to restore the immune system.

Figure 4:
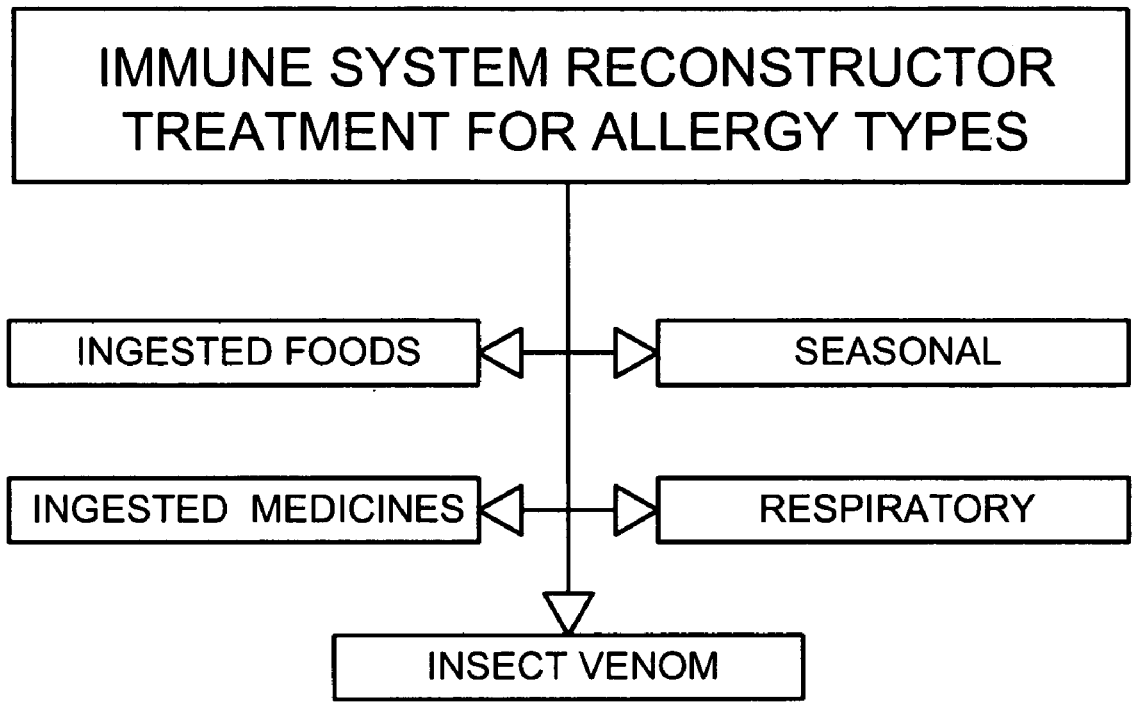
FIG. 4 is a block diagram of the present invention, immune system reconstructor treatment for allergy types.

Referring to FIG. 4, shown is a block diagram of types of allergic reactions (56) that may benefit from the immune system reconstructor (10) of the present invention. A strong immune system is essential to protecting against and being cured from types of allergies. Seasonal and other respiratory allergies, allergies from ingested foods and medicine, as well as allergies from insect venom (bites) can be fought and cured by restoring a strong immune system. The formulation of the present invention (10) provides the user an all natural means to restore the immune system and protect against allergies.

Figure 5:
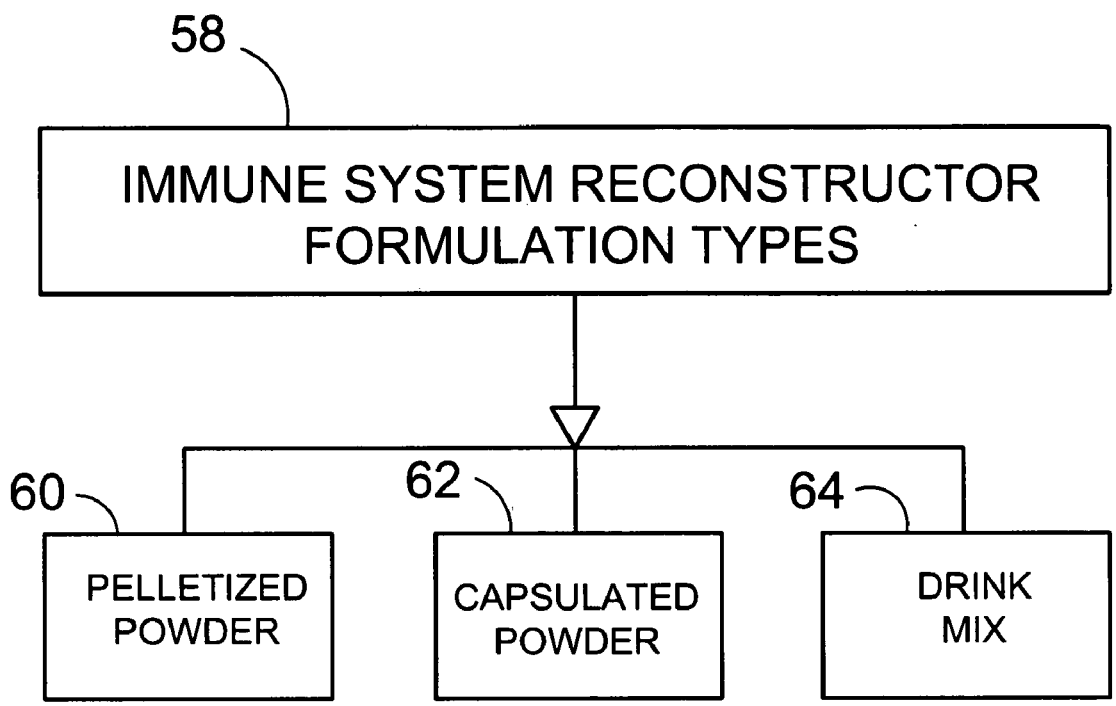
FIG. 5 is a block diagram of the present invention, immune system reconstructor formulation types.

Referring to FIG. 5, shown is a block diagram of types of packaging (58) that can be used for distribution of the immune system reconstructor (10) of the present invention. The immune system reconstructor is effective to protect against infectious diseases in any form of ingestion. To suit the user preference, the all natural formulated powder can be tabulated into a pellet (60), capsulated (62), or stirred into a drink mix (64). Natural or artificial flavoring can also be added without hindering the restoring effects the present invention has on the immune system.

Figure 6:
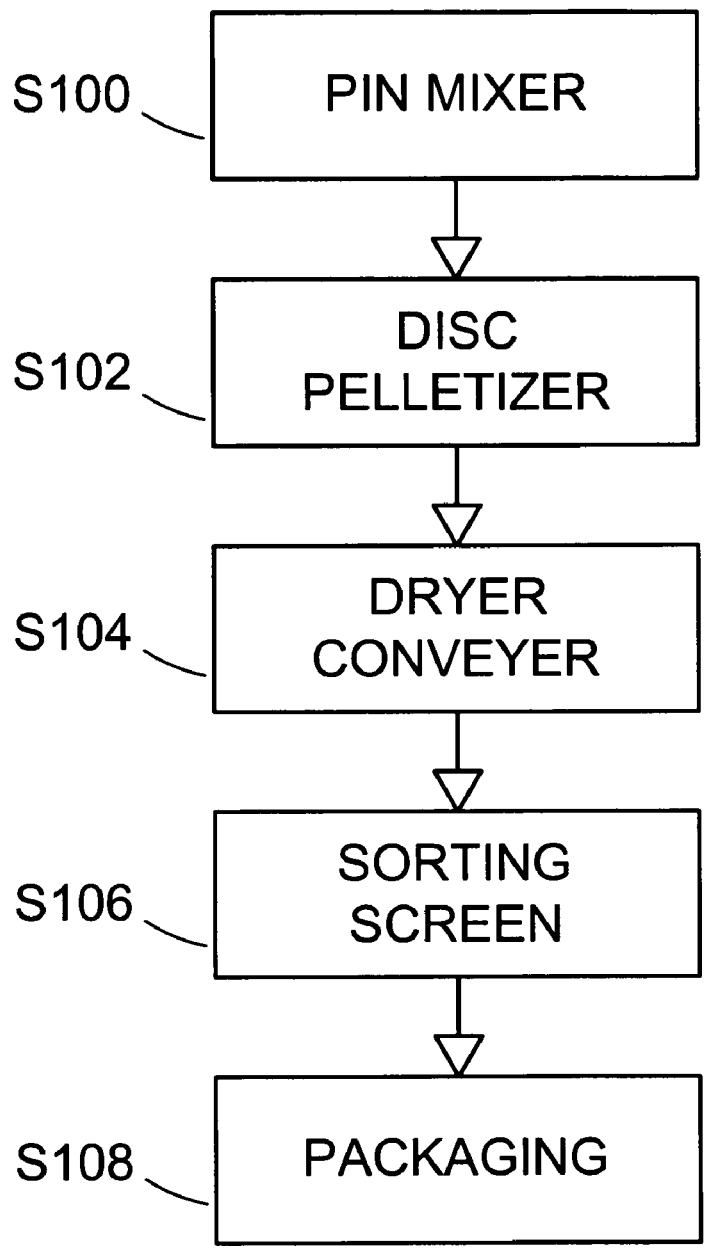
FIG. 6 is a flow chart of the present invention's pelletizing process.

Referring to FIG. 6, shown is a flow chart of the pelletizing process (60) that can be used in the preparation of the immune system reconstructor as a tablet. The pin mixer receives the premixed immune system reconstructor powder from the storage bin and feeder, as shown in step S100. Mixes the powder with a binder and sends it to the disc pelletizer as shown in step S102. The disc pelletizer turns the immune system reconstructor mix into pellets and sends them on a conveyor belt to the dryer, as shown in step S104. The dryer dries and then cools the pellets, discharging them onto a conveyor belt that carries them to the screen, as shown in step S106. The screen removes and recycles oversized and undersized pellets, sending the "good" ones to packaging, as shown in step S108. The pellets are packaged and sealed for shipment.

Figure 7:
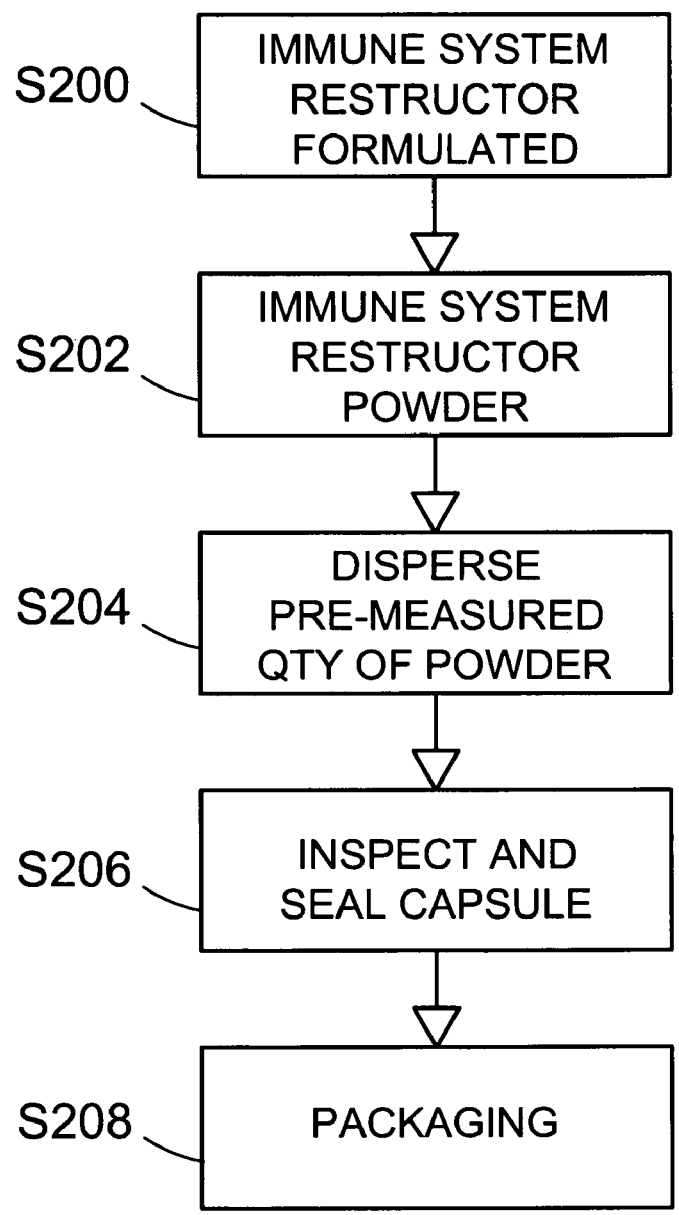
FIG. 7 is a flow chart of the present invention's capsule form process.

Referring to FIG. 7, shown is a flow chart of the encapsulation process (62) that can be used in the preparation of the immune system reconstructor (10) as a gel capsule. The immune system reconstructor is formulated, as shown in step S200. The formulation is prepared into a powder mix, as shown in step S202. A predetermined quantity of immune system reconstructor powder is dispersed into a water soluble capsule, as shown in step S204. The capsules are inspected and sealed, as shown in step S206. The immune system reconstructor capsules are packaged for consumer use, as shown in step S208

Figure 8:
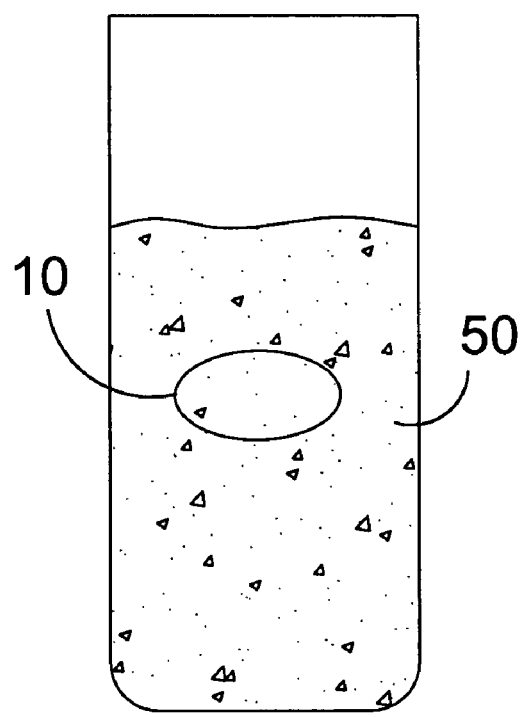
FIG. 8 is an illustrative view of the present invention, immune system reconstructor utilized in a drink mix.

Referring to FIG. 8, shown is the encapsulation process (64) used in the preparation of the immune system reconstructor (10) as a drink mix. Depicted is a pellet (60) or capsule (62) form of the immune system reconstructor (10) being dispersed in liquid water (50) to form a drink mix (64). Additional natural or artificial flavorings can be added to suit the user preference.

What is claimed as new and desired by Letters Patent of the United States is:

1. A composition for human consumption for enhancing the immune system comprising effective amounts of:
    a) carrot powder;
    b) pau d' arco bark;
    c) *gingko* leaf;
    d) myrrh bark;
    e) *echinacea* augustafolia;
    f) slippery elm bark;
    e) heal-all-herb;
    f) celery stalk;
    g) celery leaf;
    h) red clover blooms;
    i) burdock root;
    j) goldenseal root;
    k) poke root;
    l) garlic bulb powder;
    m) beet root powder;
    n) yellow dock root;
    o) dandelion root;
    p) St. John's wort; and
    q) *capsicum.*

2. The composition of claim 1, wherein said composition can be manufactured in a powder form.

3. The composition of claim 1, wherein said composition can be manufactured in capsule form.

4. The composition of claim 1, wherein said composition can be manufactured in tablet form.

5. The composition of claim 2, wherein said composition can be used in conjunction with a predetermined quantity of water to provide a drink mix.

6. The composition as recited in claim 1, wherein said composition comprises the following quantities:
    a) carrot powder—29 parts;
    b) pau d' arco bark—27 parts;
    c) *gingko* leaf—19 parts;
    d) myrrh bark—19 parts;
    e) *echinacea* augustafolia—17 parts;
    f) slippery elm bark—15 parts;
    e) heal-all-herb—15 parts;
    f) celery stalk—14 parts;
    g) celery leaf—14 parts;
    h) red clover blooms—13 parts;
    i) burdock root—11 parts;
    j) goldenseal root—10 parts;
    k) poke root—9 parts;
    l) garlic bulb powder—7 parts;
    m) beet root powder—7 parts;
    n) yellow dock root—6 parts;
    o) dandelion root—6 parts;
    p) St. John's wort—4 parts; and
    q) *capsicum*—0.5 parts.

* * * * *